United States Patent [19]

Cushing et al.

[11] 4,277,178

[45] Jul. 7, 1981

[54] WEB ELEMENT CONCENTRATION DETECTION SYSTEM

[75] Inventors: Charles J. Cushing; Clifton W. Phillips; Richard D. VanderNeut, all of Charlotte, N.C.

[73] Assignee: Ford Aerospace & Communications Corp., Detroit, Mich.

[21] Appl. No.: 112,381

[22] Filed: Jan. 15, 1980

[51] Int. Cl.$^3$ ............................................ G01N 21/86
[52] U.S. Cl. ................................... 356/431; 250/559; 250/571
[58] Field of Search ............... 250/559, 572, 571, 561, 250/563; 356/429–431

[56] References Cited

U.S. PATENT DOCUMENTS

| | | |
|---|---|---|
| 3,074,631 | 1/1963 | Buysch .................................. 356/429 |
| 3,305,687 | 2/1967 | Vinzelberg et al. ................. 250/563 |
| 3,612,702 | 10/1971 | Troll ..................................... 356/430 |
| 3,800,160 | 3/1974 | Ishizawa ............................. 250/563 |
| 3,972,624 | 8/1976 | Klein et al. .......................... 356/431 |

Primary Examiner—John R. Corbin
Assistant Examiner—Bruce Y. Arnold
Attorney, Agent, or Firm—Paul K. Godwin, Jr.; Clifford L. Sadler

[57] ABSTRACT

A flying spot scanner is utilized to scan a beam of laser radiation along a fixed spacial path on a moving web material. An optical detector assembly is positioned to receive radiation reflected from individual elements of the web to produce an electrical signal which is processed to determine and monitor the number of the individual web elements per unit length.

10 Claims, 3 Drawing Figures

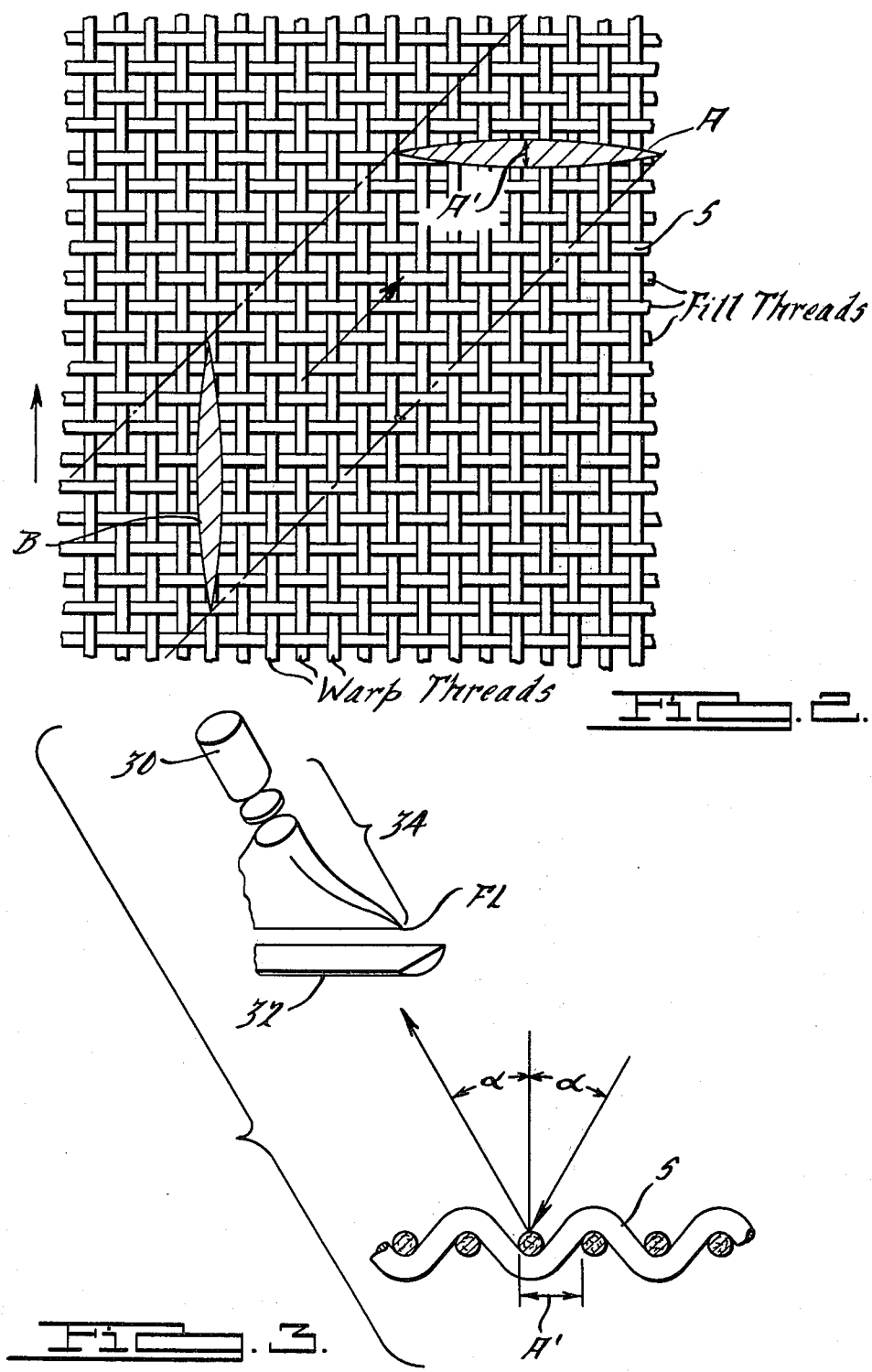

WEB ELEMENT CONCENTRATION DETECTION SYSTEM

BACKGROUND OF THE INVENTION

1. Field of the Invention

The present invention is directed to the field of optical inspection of web materials and is ideally suited for use in high production facilities where the quality of such materials is of critical importance.

2. Description of the Prior Art

In the textile industry, the quality and use of woven and non-woven material depends upon many factors which occur during the manufacture and handling of the fabric. One measure of quality is the number of fabric elements per unit length of material. In woven material, the number of warp threads per unit length is generally held constant by monitoring devices at the weaving loom. However, the number of fill threads per unit length is critical in first quality goods for particular uses and tends to vary due to tension changes that occur during the weaving operation or improper yarn size. The concentration of fill threads is generally determined in the industry by periodically sampling a small length of material and manually counting the number of fill threads. Needless to say, this is laborious, as well as time consuming and does not allow for even the hope of performing 100% inspection of the woven product.

Several automatic systems have been disclosed which measure the density, the reflectivity and the size of web material as it is transported past an inspection point. However, the measurement of the number of fabric elements per unit length continues to be performed manually.

SUMMARY OF THE INVENTION

The present invention is intended to overcome the deficiencies of the prior art by providing an automatic system for inspecting and detecting variations in the number of regularly occurring elements in a web material per unit length. The system may be employed for the inspection of woven fabric, wire screen, non-woven fabric or any other material whose construction comprises visible elements in a regular spaced pattern.

The present invention utilizes a flying spot scanner that is synchronously controlled to scan a laser generated beam of visible electromagnetic radiation along a fixed spatial path on the material to be inspected. An optical detector assembly is disposed to receive a portion of the scan radiation that is reflected from the material.

The web material is transported past the inspection point in a direction parallel to the warp threads in a woven material. In order to count the fill threads, that are ideally woven orthogonal to the warp threads, the beam is scanned along a path that is transverse to the fill threads. The fill count beam has an elongated cross section that is generally parallel to the fill threads. The width dimension of the beam cross section is selected for proper resolution and is less than the expected width of a normal fill thread combined with the expected width of the normal spacing between adjacent fill threads. As the fill count beam is scanned across the fabric, individual fill threads reflect the incident light. The optical detector assembly is fixedly disposed so as to receive light reflected from individual fill threads at a particular angle and produce an electrical signal indicative of each fill thread as it is scanned. Appropriate circuitry is included to process the detector signal and count the number of elements detected over a predetermined period of time, corresponding to a unit length of material. These counts are compared with previous measurements and a predetermined range of numbers to determine if the material contains a variation that effects quality. In a practical installation, the material may be physically marked alongside the position corresponding to the detected element concentration change. A corresponding printout would be produced to indicate the degree of change at each occurrence.

A second beam may be scanned over the material to count the number of warp threads per unit length. The warp count beam follows the same path as the fill count beam, but has an elongated cross section that is generally parallel to the warp threads. The width of the warp count beam cross section is also pre-selected to produce high resolution at the detector.

It is an object of the present invention to provide an automatic system to measure the concentration of elements in a web material.

It is another object of the present invention to provide a system which automatically scans a woven web material and continually monitors the number of fill elements per unit length over its entire length.

It is a further object of the present invention to provide an automatic system which has the capability of providing a 100% inspection of a transported web material to monitor the concentration of regularly spaced elements over the width and length of the material.

BRIEF DESCRIPTION OF THE DRAWINGS

FIG. 2 is a top view of a scanned web material.

FIG. 3 is a side view of the scanned web material illustrating an optical detector assembly positioned to receive a portion of the scanned beam reflected from the web material.

DESCRIPTION OF THE PREFERRED EMBODIMENT

Figure 1:
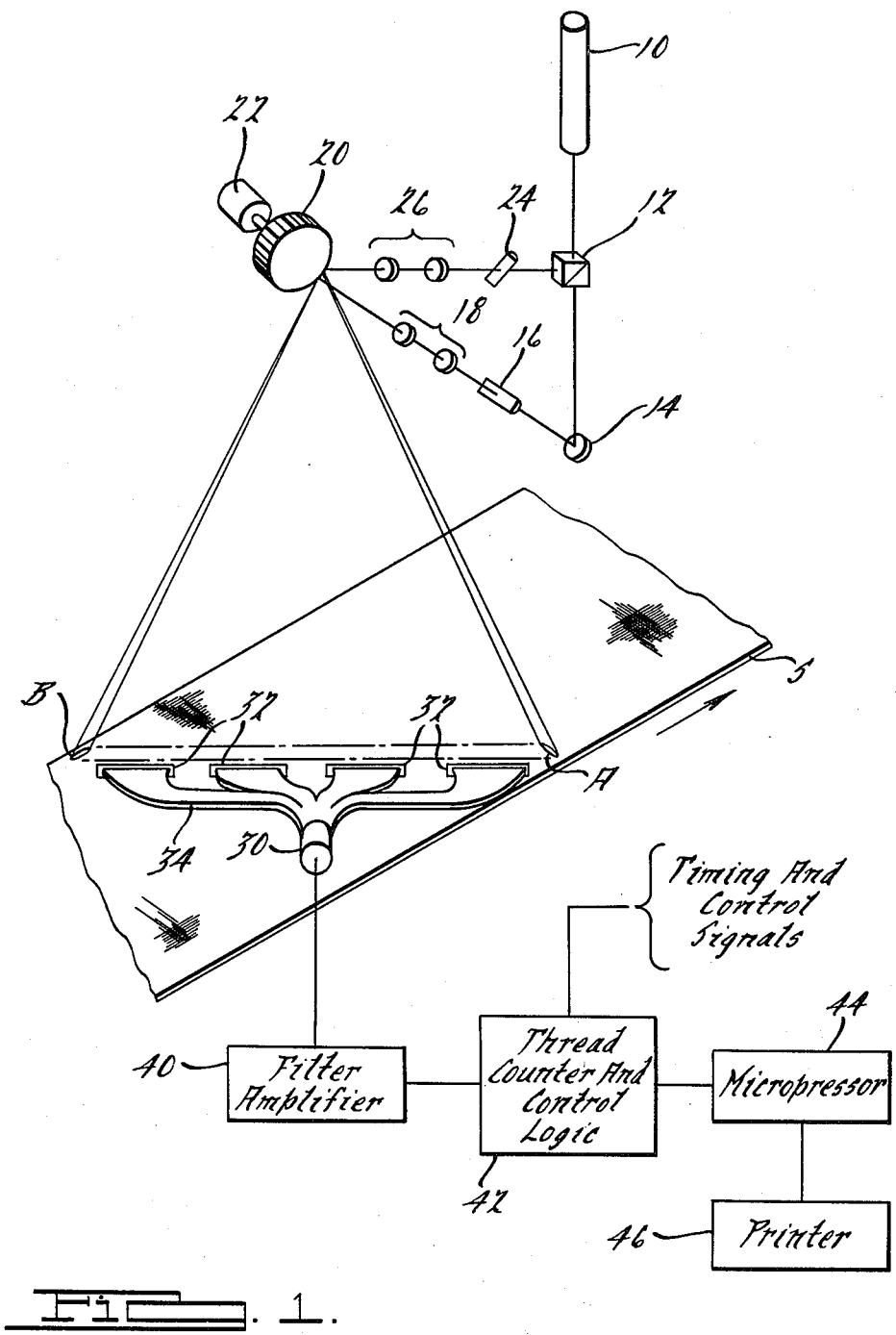
FIG. 1 is an overall view of the present invention.

The following discussion co-references FIGS. 1, 2 and 3, which contain like reference characters to indicate the same elements in each figure.

The preferred embodiment of the present invention is incorporated in a textile scanning system which employs alternately scanned beams having elongated cross-sections. The alternately scanned beams are orthogonally oriented with respect to each other and are respectively generally parallel to the warp and fill threads of the woven material being sampled.

In the preferred embodiment, a woven web material S is transported in the direction of the arrows shown in FIGS. 1 and 2 by a high speed transport mechanism (not shown) of conventional design. The web material S has been transported at a speed of approximately 250 yds./min. with a high degree of accuracy resulting from the element counting portion of the present invention. However, slower or faster transport speeds may be utilized as dictated by the particular fabric and resolution capabilities of the constructed system.

A flying spot scanner is employed which, in this case, provides scanning beams which repeatedly traverse a fixed spatial path at a frequency of approximately 1000 scans/sec. on the upper surface of the web transported material S.

The flying spot scanner, of the preferred embodiment, produces two sequentially scanned beams A and B having orthogonally oriented elongated cross-sections. The beams are preferably generated by splitting a single beam from a laser generator 10 with a beam splitter 12. The split beams are respectively directed through an anamorphic lens system and to a rotating multifaceted scanning mirror 20. The speed of rotation of the multifaceted scanner 20 is a constant, controlled by a synchronous motor 22.

In the case of scan beam A, which has an elongated cross section generally parallel to the fill elements of the web material, the beam is reflected from the beam splitter 12 and then reformed and focused by an anamorphic lens system which includes cylindrical lens 24 and lens elements 26. As the multifaceted mirror 20 rotates, beam A is scanned across the fixed spatial path, which is approximately 45° with respect to the direction of movement of the web material S. The beam A is formed so as to give a high reflection intensity when it is incident upon the fill threads which are expected to be parallel to the beam A elongation. Therefore, with the scan beam incident at an angle $\alpha$, radiation is reflectively scattered due to the shape of the fill threads. In this embodiment, an optical detector assembly is positioned to receive all light reflected from the fill threads within its field of view at an angle $\alpha$ with respect to the normal. The optical detector assembly includes a plurality of cylindrical lenses 32 spaced parallel to the spatial scan path so as to focus any light received thereby onto a focal line FL. A fiberoptic line-to-spot bundle 34 is disposed so as to have one end extending along the focal line FL of the cylindrical lens 32 and the other end appropriately bundled to be opposite a photosensitive detector 30. A notch filter may be employed between the fiberoptic bundle and the photosensitive detector in order to insure that the photosensitive detector only receives radiation of the frequency generated by the laser 10. Such a notch filter reduces the effects of stray light which may be incident onto the web material.

The width dimension A' of the fill scanned beam A is selected to give a high resolution. The value of A' is selected to be less than the expected thickness of a normal fill thread plus the expected distance between adjacent fill threads.

The photosensitive detector 30 is electrically connected to a filter amplifier 40 which further removes noise from the electrical signal and produces pulses which correspond to each detection of a fill thread during the scan of the A beam. The pulses are then counted by a thread counter and control logic circuit 42 in response to timing and control signals which appropriately dictate that portion of the web material S selected to be sampled for each scan. An appropriately programmed microprocessor 44 is employed to compare the sampled thread count with previous samplings and predetermined error values in order to determine whether the sample count is within the acceptable range. The microprocessor 44 causes an appropriate indication to be made as to the location of the concentration change and its duration to a printer 46. The printer, of course, is used to produce a permanent recording to indicate the location of flaws detected in the material and allow the operator to judge the quality of the material and determine any cutting requirements that may be necessitated.

After a total sweep of the beam A, the flying spot scanner sweeps a beam B over the same spatially located scan path. Since the warp threads of the woven material are orthogonal to the fill threads, the beam B is orthogonally elongated with respect to the beam A. Of course its width is selected for high resolution and reflective incident radiation therefrom is received by the same optical detector assembly. The beam B is formed by the radiation which is transmitted through the beam splitter 12, reflected from a front surface mirror 14, and focused by a cylindrical lens 16 and lens 18 before being incident upon another facet of the multifaceted mirror scanner 20. The arrangement of the optics of the flying spot scanner guarantees that the two beams A and B are alternately and separately scanned over the material. A separate detector (not shown) within the scanner functions to produce a timing signal to the control circuitry indicating which beam is being scanned across the material at any time. Therefore, the sensed information is discernible by the microprocessor as to whether it is a measure of warp or fill thread counts per unit length of material.

It will be apparent that many modifications and variations may be effected without departing from the scope of the novel concept of this invention. Therefore, it is intended by the appended claims to cover all such modifications and variations which fall within the true spirit and scope of the invention.

What is claimed is:

1. A system for detecting variations in the concentration of elements in a web material comprising:
   means for generating plural beams of electromagnetic radiation having a predetermined cross-sectional width;
   means for scanning said beams across a portion of said web material; and
   means for detecting said radiation reflected from said scan portion of said web material by said elements of said web material.

2. A system as in claim 1, wherein said web material is woven with warp and fill elements and said system detects variations in the number of each of said elements counted over a predetermined distance of said material.

3. A system as in claims 1 or 2, wherein said predetermined width of said scanned radiation at said web is less than the expected width of the elements combined with the expected distance between adjacent elements.

4. A system as in claim 1, wherein said web material is woven with warp and fill elements and said system detects variations in the number of fill elements over a predetermined distance in said material.

5. A system as in claim 2, wherein said generating means includes a visible wavelength laser and said scanning means includes a multifaceted mirror drum for receiving said radiation from said laser and repeatedly reflecting said radiation onto the same spatial path location at said material transverse to both said warp and fill elements.

6. A system as in claims 2 or 5 wherein said detecting means includes a cylindrical lens located to receive and focus a portion of said radiation reflected from said material, a photosensitive detector responsive to changes in the intensity of said radiation by producing an electrical output signal indicative of those changes and positioned to receive said reflected radiation portion focused by said cylindrical lens and an optical means for transmitting said focused reflected radiation to said photosensitive detector.

7. A system as in claim 6, wherein said detecting means includes means for monitoring said electrical output signal to count the number of fill elements being scanned over a predetermined period of time.

8. A system as in claim 2, wherein said detecting means includes means for monitoring said electrical output signal to count the number of fill elements being scanned over a predetermined period of time.

9. A system as in claim 8, further including means to transport said web material along a linear path transverse to said beam scanning path.

10. A system as in claim 9, wherein said web transport path and said beam scanning path at said web form an intersection angle of approximately 45°.

* * * * *